United States Patent [19]

Fujishima

[11] Patent Number: 4,594,320
[45] Date of Patent: Jun. 10, 1986

[54] PROCESS FOR PRODUCING 3-DEOXYGUANOSINE

[75] Inventor: Tetsuro Fujishima, Choshi, Japan

[73] Assignee: Yamasa Shoyu Kabushiki Kaisha, Choshi, Japan

[21] Appl. No.: 479,980

[22] Filed: Mar. 29, 1983

[30] Foreign Application Priority Data

Nov. 4, 1982 [JP] Japan .................................. 57-194394

[51] Int. Cl.$^4$ ...................... C12R 1/265; C12R 1/445; C12R 1/45; C12R 1/64; C12P 19/30; C12P 19/38; C12P 19/40; C12N 9/12
[52] U.S. Cl. .......................................... 435/89; 435/87; 435/88; 435/194; 435/859; 435/883; 435/884; 435/910
[58] Field of Search ..................... 435/87, 88, 89, 193, 435/194, 859, 883, 884, 910

[56] References Cited

U.S. PATENT DOCUMENTS 3,269,917  8/1966  Imada et al. .......................... 435/88
3,763,008 10/1973  Nakayama et al. ................... 435/87
4,381,344  4/1983  Rideout et al. ........................ 435/87

OTHER PUBLICATIONS

Tarr, H. L. A., *Methods in Enzymology*, vol. XII, Part A, pp. 113–118, 1968.
The Condensed Chemical Dictionary, 5th Ed., Reinhold Publishing Corp., pp. 348–349, 792–793, 1956.

*Primary Examiner*—Thomas G. Wiseman
*Assistant Examiner*—Jayme A. Huleatt
*Attorney, Agent, or Firm*—Wenderoth, Lind & Ponack

[57] ABSTRACT

Glycosylation or transglycosylation of a specified guanine derivative, namely 9-substituted or non-substituted guanine of formula [I] with a 3-deoxyribose donor such as 3'-deoxyadenosine in the presence of a nucleoside phosphorylase source such as of microorganism origin is disclosed. The nucleoside phosphorylase source is specified.

6 Claims, No Drawings

PROCESS FOR PRODUCING 3-DEOXYGUANOSINE

BACKGROUND OF THE INVENTION

This invention relates to an enzymatic process for producing 3'-deocxyguanosine.

3'-Deoxyguanosine is a compound presently attracting attention which not only exhibits radiation sensitizing action in therapy of cancers but also has an action to enhance the effect of various anticancer agents when employed in combination therewith (see Japanese Laid-open Publication No. 35516/1982).

In the prior art, as the method for preparation of 3'-deoxyguanosine, is known the method in which a chloromercuri of 2-acetamidohypoxanthine is condensed with 2,5-di-O-benzoyl-3-deoxy-D-ribofuranosyl bromide [The Journal of Organic Chemistry, 30, 2851 (1965)]. However, this method is believed to involve various drawbacks in commercial production such as, for example, difficult availability of the starting material 3-deoxyribose, formation of isomers during the condensation reaction, use of a harmful mercuric salt, and others.

SUMMARY OF THE INVENTION

The present inventors have made various investigations in order to overcome these drawbacks of the prior art and consequently found that 3'-deoxyguanosine can be formed by causing a guanine derivative to react with a 3'-deoxyribose donor in the presence of a nucleoside phosphorylase source. The present invention has been accomplished based on such a finding.

The present invention provides a process for producing 3'-deoxyguanosine, which comprises causing a guanine derivative represented by the formula [I]:

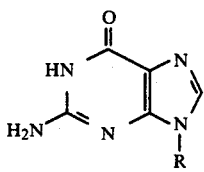

wherein R designates a hydrogen atom or a ribose-1-yl group, a 2-deoxyribose-1-ly group or a monophosphate, a diphosphate or a triphosphate thereof, to react with a 3-deoxyribose donor in the presence of a nucleoside phosphorylase source derived from a microorganism which belongs to a genus Xanthomonas, Micrococcus, Staphylococcus or Sarcina to obtain 3'-deoxyguanosine.

DETAILED DESCRIPTION OF THE INVENTION

The present invention is to be described in detail below.

Guanine derivative

As the starting guanine derivatives, there may be employed one or more of the compounds included within the aforementioned definition. More specifically, illustrative of these compounds are guanine (Gua), guanosine (Guo) or 2'-deoxyguanosine (2'-dGuo) or monophosphates, diphosphates or triphosphates thereof. The above nucleotide may have a phosphoryl group at any position of hydroxyl groups in the sugar residue. Typical examples of these nucleotides may include guanosine-5'-monophosphate (GMP), guanosine-3'-monophosphate, guanosine-2'-monophosphate, guanosine-5'-diphosphate (GDP), guanosine-5'-triphosphate (GTP), 2'-deoxyguanosine-5'-monophosphate (2'-dGMP), 2'-deoxyguanosine-3'-monophosphate, 2'-deoxyguanosine-5'-diphosphate (2'-dGDP), 2'-deoxyguanosine-5'-triphosphate (2'-dGTP) and the like, which may be either in free acid form or in an appropriate salt form such as sodium salt.

3-Deoxyribose donor

As the other starting material, a 3-deoxyribose donor, there may be employed any compounds which are capable of enzymatically introducing 3-deoxyribose moiety to the 9-position of the guanine moiety of the compound of formula [I] through direct glycosylation or transglycosylation. Typical examples include one or more of 3'-deoxyadenosine (3'-dAdo; cordycepin), 3'-deoxyinosine (3'-dIno), or monophosphates, diphosphates or triphosphates thereof, or 3-deoxyribose-1-monophosphate. The above phosphates may have phosphoryl group at any position of hydroxyl group in 3-deoxyribose, and may also be either in free acid form or in a salt form. Illustrative of these nucleotides are 3'-deoxyadenosine-5'-monophosphate (3'-dAMP), 3'-deoxyinosine-5'-monophosphate (3'-dIMP) or 3-deoxyribose-1-phosphate.

Nucleoside phosphorylase source

The nucleoside phosphorylase which is in the nucleoside phosphorylase source in the reaction of the present invention refers comprehensively to a single enzyme or a plurality of enzymes capable of providing 3'-deoxyguanosine by causing the guanine derivative to react with the 3-deoxyribose donor in the presence of a phosphoric acid ion donor. Accordingly, in the present invention, the term "nucleoside phosphorylase source" includes the enzymes of the phosphorylase type such as purine nucleoside phosphorylase, pyrimidine nucleoside phosphorylase, etc., which can be used in combination with enzymes such as nucleoside-N-glycosyl transferase, nucleosidase, nucleotidase, phosphatase and others, which may possibly participate in the reaction of the present invention. The nucleoside phosphorylase source refers comprehensively to a material containing such enzymes in any desired form, which is derived from a specific group of microorganisms, namely those belonging to a genus Xanthomonas, Micrococcus, Staphylococcus or Sarcina. In particular, a nucleoside phosphorylase source in the form of a culture, a mass of intact cells or a modification of cells of a microorganism, is preferred.

Typical strains of such microorganisms are:
X. campestris: IAM 1671, ATCC 7381 (FERM P-6782)
M. luteus: ATCC 4698, IAM 1056
St. aureus: IAM 1011, ATCC 6538P
St aureus: IFP 3060
St. epidermidis: IFO 3762, ATCC 155
Sa. marginata: FERM P-6539.
(X: Xanthomonas; M: Micrococcus; St: Staphylococcus; and Sa: Sarcina).

The mutant strains derived from the above microorganism strains through induced mutation according to the mutagenic methods in general by a physical treatment such as irradiation of UV-ray, X-ray or γ-ray or a chemical treatment with nitrosoguanidine or other mutagens or natural mutation attributable to natural causes may be also available in the present invention, so long as they do not lose the ability to produce nucleoside phosphorylase source suitable for the object of the present invention.

Further, when the gene for nucleoside phosphorylase source suitable for the object of the present invention of the microorganism strains preferably used in the present invention as described above is integrated in a microorganism other than the genera Xanthomonas, Micrococcus, Staphylococcus and Sarcina if the characteristic of such a gene is phenotypically expressed, the method of employing the culture, the intact cells of such a microorganism or the modification thereof for the object of the present invention may also be included within the present invention.

In cultivation of these microorganisms to produce a nucleoside phosphorylase source, the culture medium and the method of culture employed are not particularly limited, so far as growth of these microorganisms is concerned.

As a culture medium, there may be employed one containing appropriate amounts of a carbon source and a nitrogen source assimilable by these microorganisms, optionally added with an inorganic salt, minute amounts of a growth promoter, defoaming agents, etc. More specifically, as carbon sources, there may be employed one or more of those selected suitably in view of assimilability by the microorganism employed from carbon sources in general, including sugars such as glucose, fructose, maltose, galactose, ribose, saccharose, starch, starch hydrolysate, molasses, waste molasses, etc. or derivatives thereof such as fatty acid esters thereof; natural carbohydrates such as what, wheat bran, rice, etc.; alcohols such as glycerol, mannitol, methanol, ethanol, etc.; fatty acids such as gluconic aicd, pyruvic acid, acetic acid, citric acid, etc.; hydrocarbons such as normal paraffins, kerosene, etc.; amino acids such as glycine, glutamic acid, glutamine, alanine, asparagine, etc.; and so on. As nitrogen sources, there may be employed one or more of those selected suitably in view of assimilability by the microorganism employed from nitrogen sources in general, including organic nitrogenous materials such as meat extract (bouillon), peptone, yeast extract, dry yeast, soybean hydrolysate, soybean powder, milk casein, casamino acid, various amino acids, corn steep liquor, cotton seed meal or its hydrolysate, fish meal or its hydrolysate, hydrolysates of other animals, vegetables, microorganisms, etc.; inorganic nitrogen compounds such as ammonia, ammonium salts such as ammonium nitrate, ammonium sulfate, ammonium chloride, ammonium phosphate, ammonium carbonate, ammonium acetate and the like, nitric acid salts such as sodium nitrate, urea, and so on. Further, as inorganic salts, there may suitably be added one or more, in minute amounts, of phosphates, hydrochlorides, sulfates, carbonates, nitrates, acetates and others of magnesium, manganese, iron, zinc, copper, sodium, calcium, potassium, etc. If necessary, there may also be added a defoaming agent such as a vegetable oil or a surfactant, a minute amount of a growth promoter such as vitamins $B_1$, $B_2$, nicotinic acid, pantothenic acid, biotin, P-aminobenzoic acid, etc. When employing a microorganism exhibiting nutrient requirements, substances satisfying its growth must be added into the culture medium as a matter of course.

Cultivation may be performed in a liquid medium containing the above culture medium components by selecting a culture method suitable for the microorganism employed from conventional culture methods such as shaking culture, aerating stirring culture, stationary culture, continuous culture and others.

The cultural conditions may be suitably chosen depending on the microorganism and the culture medium employed, but generally by adjusting before start-up of cultivation at pH of about 6 to 8 and carrying out cultivation under the temperature condition of about 25° to 35° C. The culture duration may be a period sufficient for growth of the microorganism employed, being generally 1 to 3 days.

After culturing the microorganism as described above, the culture, the intact microbial cells collected from the culture according to a conventional method such as centrifugation, sedimentation separation, agglomeration separation, or a modification of microbial cells obtained by applying a suitable treatment on the living or intact cells may be used as the nucleoside phosphorylase source of the present invention. The "culture" herein refers to a product under the state where the culture medium and the cultured microbial cells after cultivation are still unseparated from each other. The "modification of cells" refers to dried microbial cells, microbial cells whose cell wall membrane having been modified, crushed microbial cells, immobilized microbial cells, extracts of microbial cells, protein fractions having nucleoside phosphorylase activity of extract of microbial cells or purified product thereof, immobilized product of the protein fractions or purified product thereof, and the like. Methods for obtaining the modification of microbial cells are to be illustrated below. Modifications of microbial cells can be obtained by applying on intact microbial cells singly or in combination physical treatment means such as freezing-thawing, lyophilization, air drying, acetone drying, heating under acidic or alkaline conditions, grinding, ultrasonic treatment, osmotic treatment, etc. or chemical or biochemical treatments such as enzymatic treatments with lysozyme, cell wall lysing enzymes, etc., contact treatments with solvents such as toluene, xylene, butyl alcohol or surfactants, or by applying on the extract of microbial cells singly or in combination enzyme separation and purification means such as salting-out, isoelectric precipitation, precipitation with organic solvents, various chromatographies, dialysis and others, or further by applying on intact microbial cells, extracts of microbial cells or purified products thereof an enzyme or cell immobilization means such as inclusion method, cross-linking method, adsorption method onto a carrier, etc.

Glycosylation or transglycosylation

The reaction in accordance with the present invention, namely enzymatic reaction of a guanine derivative of formula [I] with a 3-deoxyribose donor, which is glycosylation when the substituent R is hydrogen and is otherwise transglycosylation, is carried out by bringing a guanine derivative and a 3-deoxyribose donor into contact with the nucleoside phosphorylase source as described above in an aqueous medium. The kinds of the enzyme substrates are selected according to the kind of the enzyme source employed.

In a preferred embodiment of the present invention, there are two methods available to effect the contact.

The first method is one in which a guanine derivative and a 3-deoxyribose donor are caused to be present in the culture medium during cultivation of the aforesaid microorganism, thereby accumulating 3'-deoxyguanosine in the culture medium.

The above method may be carried out by adding necessary amounts of a guanine derivative and a 3-deoxyribese donor in the culture medium prior to cultivation and cultivating the microorganism therein, or by adding these substances at once at an appropriate period of time during cultivation, or by carrying out cultivation while adding intermittently or continuously these substances.

The second method may be carried out by bringing a culture, intact microbial cells or a modification of cells into contact with an aqueous medium containing a guanine derivative and a 3-deoxyribose donor under the conditions capable of forming 3'-deoxyguanosine.

An aqueous medium in which the contact between the reactants concerned is to take place may be water or various buffers preferred for enzymatic reactions (e.g. phosphate buffers, imidazole-hydrochloric acid buffer, veronal-hydrochloric acid buffer, Tris-hydrochloric acid buffer), which contains a phosphate ion generating source and may also contain various substances, if desired.

The enzymatic reaction of the present invention is mainly based on the action of phosphorylase, and therefore a phosphate ion must exist in the reaction system. In the case where a phosphate ion does not exist in the reaction system, an addition of a phosphate ion generating substance is necessary. As the phosphate ion generating substance, there may be employed any compound dissociable into phosphate ion in an aqueous medium, such as phosphoric acid itself, inorganic phosphoric acid salts such as salts of alkali metals, for example, sodium, potassium and the like, alkaline earth metals, for example, calcium, magnesium and the like or ammonium. These phosphate generating sources may be employed in amounts of about 1.0 to 2.5-fold moles per mole as phosphate ions per mole of the guanine derivative. As substances other than the phosphate ion generating source which may be contained in the aqueous medium, there may be employed sugars such as glucose, sacchrose and the like, organic solvents such as methanol, ethanol, propanol, butanol, pentanol, toluene, xylene, ethyl acetate and the like, various surfactants, metal salts and so on.

As the method to bring a nucleoside phosphorylase source into contact with a guanine derivative and a 3-deoxyribose donor in an aqueous medium, there may be employed the method in which the nucleoside phosphorylase source is suspended or dissolved in an aqueous medium containing these reaction substrates, optionally with stirring or shaking, or the method in which these reaction substrates are added at once, intermittently or continuously into a suspension or a solution of the nucleoside phosphorylase source in a reaction medium, or the method in which the nucleoside phosphorylase source is packed in a column optionally admixed with a suitable diluent or carrier or immobilized onto a membrane and an aqueous medium containing the reaction substrates is passed therethrough.

During the reaction, the substrate concentration is not particularly limited, and the reaction may be carried out under a suspended state of the substrates. But each reaction substrate is used usually at a concentration within the range from 5 to 50 mM, preferably about 15 to 35 mM for a guanine derivative and about 15 to 30 mM for 3-deoxyribose donor. The nucleoside phosphorylase source may be employed in an amount, which can easily be determined by those skilled in the art by considering the particular source material employed, the concentrations of the reaction substrates, the reaction efficiency and economy.

The reaction conditions, which are not particularly limited and may be determined while considering the optimum temperature and the optimum pH for the enzymatic action of the nucleoside phosphorylase source, stability of the substrates and reaction efficiency, may generally comprise a temperature of 40° to 75° C., preferably 50° to 70° C. and a pH 5.0 to 9.0, preferably 6.0 to 8.0. When pH is changed during the reaction, an acid or an alkali can be used to correct the pH to a preferred level.

The reaction time, which may be determined while confirming the conversion of the reaction substrates to the desired product, may be generally about 15 to 45 hours, preferably 24 to 36 hours, in a batch system. In a columnar system, the reaction may be carried out under appropriate conditions set analogously as in the batch system.

After the enzymatic reaction, the nucleoside phosphorylase source may be removed by separation in a conventional manner, and the residual product is subjected to the step for isolation and purification of 3'-deoxyguanosine.

Isolation and purification of 3'-deoxyguanosine may be performed according to any of the methods known in the art by using separation/purification methods singly or in combination such as various chromatographies, for example, ion-exchange chromatography, adsorption chromatography, partition chromatography, gel filtration, etc., the counter-current partition method, the recrystallization method and others.

EXAMPLES OF THE PREFERRED EMBODIMENTS

The present invention is to be described in further detail below by referring to Examples, each of which is illustrative of an embodiment of the present invention and not limitative of the scope of the present invention. In Examples, analysis of 3'-deoxyguanosine was conducted by high performance liquid chromatography. When analyzed by means of the device and under the conditions shown below, 3'-deoxyguanosine is eluted at a retention time around 12.90 minutes and its quantity can be calculated from the calibration curve.

Device: Shimadzu High Performance Liquid Chromatograph LC-3A model (produced by Shimadzu Corporation)
Column: Sorbax ODS, 4.6 mm×250 mm (Shimadzu Du Pont Co.)
Eluant: 20 mM Tris-hydrochloric acid buffer containing 5% acetonitrile (pH 7.5)
Flow rate: 1 ml/minute
Column operation temperature: room temperature

EXAMPLE 1

One liter of a 2% bouillon culture medium were sterilized at 120° C. for 15 minutes and cooled. Then, 50 ml of a previously precultured culture broth of *Staphylococcus aureus* IAM 1011 was added to the culture broth and cultivation was carried out at 28° C. for 22 hours. After completion of the cultivation, the cells were collected by centrifugation and a sterilized water was added to prepare 100 ml of a cell suspension.

After 502.5 mg of 3'-dAdo, 849.7 mg of guanosine and 272.0 mg of monopotassium dihydrogen phosphate were dissolved in a water under heating, the solution was made up to 100 ml (pH 7.0) and 100 ml of the above cell suspension was added thereto, followed by the reaction which was carried out at 55° C. for 72 hours. After the reaction, the cells were removed by centrifugation and the reaction product was analyzed by high performance liquid chromatography to show that the yield of 3'-deoxyguanosine was 52.44%.

The reaction mixture after removal of the cells was diluted to 1000 ml (pH 9.0), treated with an anion exchange resin "Diaion SA-12A" (trade name; produced by Mitsubishi Kasei Kogyo Co., Ltd.) (borate form) and the solution which had passed through the column and the water washings were combined and adsorbed on a cation exchange resin "Diaion PK-216" (trade name; produced by Mitsubishi Kasei Kogyo Co., Ltd.) (free acid form), followed by elution, to obtain the fractions of 3'-deoxyguanosine. These fractions were neutralized, concentrated and cooled. The crude crystals precipitated were recrystallized from hot water to obtain 198.15 mg of 3'-deoxyguanosine crystals.

EXAMPLE 2

The reactions were carried out by use of various guanine derivatives and 3'-dAdo or 3'-Ino as substrates and the same cell suspension as used in Example 1 as the enzyme source.

With the use of each 1 ml of an aqueous solution containing 20 mM 3-deoxyribose donor, 30 mM of a guanine derivative and 20 mM monopotassium dihydrogen phosphate, with addition of each 1 ml of the microbial cell suspension, the reaction was carried out at 55° C., at pH 7.0 for 70 hours. After the reaction, the microbial cells were removed by centrifugation from the reaction mixture, and the quantity of 3'-deoxyguanosine was measured and the yield was calculated to show the results as shown in Table 1.

TABLE 1

| Substrate | | 3'-deoxyguano- |
|---|---|---|
| 3-Deoxyribose donor | Guanine derivative | sine yield (%) |
| 3'-dAdo | Gua | 25.4 |
| | Guo | 50.61 |
| | GMP | 34.57 |
| | GDP | 64.76 |
| | GTP | 34.55 |
| | 2'-dGuo | 60.95 |
| | 2'-dGMP | 72.30 |
| 3'-dAdo | Gua | 8.37 |
| | Guo | 31.03 |
| | GMP | 22.11 |
| | GDP | 26.00 |
| | GTP | 13.22 |
| | 2'-dGuo | 37.01 |
| | 2'dGMP | 32.96 |

EXAMPLE 3

Various microorganisms as shown in Table 2 were cultured similarly as in Example 1, and the cultured microbial cells were collected to obtain cell suspensions similar to that in Example 1.

With the use of each 1 ml of an aqueous solution containing 20 mM of 3'-dAdo, 30 mM of GMP and 4 mM of monopotassium dihydrogen phosphate as the substrate solution, with addition of each 1 ml of the above cell suspensions, the reaction was carried out at 60° C., at pH 7.0, for 20 hours. The yields of 3'-deoxyguanosine formed were calculated similarly as described above to obtain the results as shown in Table 2.

TABLE 2

| Name of microorganism | 3'-Deoxyguanosine yield (%) |
|---|---|
| X. campestris IAM 1671 (FERM P-6782) | 9.82 |
| M. luteus ATCC 4698 | 3.06 |
| St. aureus IFO 3060 | 16.48 |
| St. epidermidis IFO 3762 (ATCC 155) | 15.02 |
| Sa. marginata (FERM P-6539) | 3.14 |

What is claimed is:

1. A process for producing 3'-deoxyguanosine, which comprises reacting a guanine derivative represented by the formula:

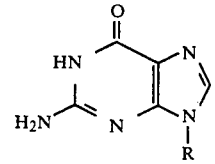

wherein R is selected from the group consisting of a hydrogen atom, a ribose-1-ly group, a 2-deoxyribose-1-yl group and a monophosphate, a diphosphate or a triphosphate thereof with a 3-deoxyribose donor at a reaction temperature of 40° to 75° C. and at a pH of 5.0 to 9.0, said reaction being carried out in the presence of a nucleoside phosphorylase source in the presence of a phosphoric acid ion donor, which source is capable of providing 3'-deoxyguanosine by the reaction of the guanine derivative with the 3-deoxyribose donor in the presence of a phosphoric acid ion donor and which nucleoside phosphorylase source is derived from a microorganism which belongs to a genus Xanthomonas, Micrococcus, Staphylococcusus or Sarcina to obtain 3'-deoxyguanosine.

2. A process for producing 3'-deoxyguanosine according to claim 1, wherein the 3-deoxyribose donor is selected from the group consisting of 3'-deoxyadenosine, 3'-deoxyinosine, and mono-, di- and triphosphates thereof and 3-deoxyribose-1-phosphate.

3. A process for producing 3'-deoxyguanosine according to claim 1, wherein the nucleoside phosphorylase source is a culture, intact cells or modified cells of a microorganism which belongs to a genus Xanthomonas, Micrococcus, Staphylococcus or Sarcina and is capable of producing 3'-deoxyguanosine from the guanine derivative of the formula [I] and the 3-deoxyribose donor, said modified cells being dried cells, cells having denatured cell membranes, cells having denatured cell walls, crushed cells, immobilized cells, or enzymatically active cells.

4. A process for producing 3'-deoxyguanosine according to claim 1, wherein the guanine derivative is guanine, guanosine, 2'-deoxyguanosine, guanosine-5'-monophosphate, guanosine-5'-diphosphate, guanosine-5'-triphosphate or 2'-deoxyguanosine-5'-monophosphate.

5. A process according to claim 1 wherein the microorganism belonging to the genus Xanthomonas, Micrococcus, Staphylococcus or Sarcina is X. campestris, M. luteus, St. aureus, or Sa. marginata.

6. A process according to claim 5 wherein the microorgansim is selected from the group consisting of X. campestris ATCC 7381, M. luteus ATCC 4698, St. aureus IFP 3060, St. aureus ATCC 6538P, St. epidermidis ATCC 155 and Sa. marginata FERM P-6539 or a microorganism derived therefrom having an ability to produce the nucleoside phosphorylase source.

* * * * *